United States Patent [19]

Javitt

[11] Patent Number: 5,587,368

[45] Date of Patent: *Dec. 24, 1996

[54] ADMINISTRATION OF A 27-HYDROXYCHOLESTEROL OR RELATED COMPOUND OR STEROL-27-HYDROXYLASE STIMULANT TO PREVENT RESTENOSIS FOLLOWING VASCULAR ENDOTHELIAL INJURY

[75] Inventor: Norman B. Javitt, New York, N.Y.

[73] Assignee: New York University, New York, N.Y.

[*] Notice: The term of this patent shall not extend beyond the expiration date of Pat. No. 5,376,652.

[21] Appl. No.: 319,225

[22] Filed: Oct. 6, 1994

Related U.S. Application Data

[63] Continuation-in-part of Ser. No. 159,226, Nov. 30, 1993, Pat. No. 5,376,652.

[51] Int. Cl.⁶ .................................................. A61K 31/56
[52] U.S. Cl. ........................ 514/177; 514/169; 514/178; 514/188
[58] Field of Search .................................. 514/177, 178, 514/188, 169

[56] References Cited

U.S. PATENT DOCUMENTS 5,376,652  12/1994  Javitt ........................................ 514/575

FOREIGN PATENT DOCUMENTS 319206  3/1994  Japan .

*Primary Examiner*—Gary Geist
*Assistant Examiner*—Dwayne C. Jones
*Attorney, Agent, or Firm*—Sughrue, Mion, Zinn, Macpeak & Seas

[57] ABSTRACT

A method for preventing or reducing restenosis wherein a 27-hydroxycholesterol or a 25,26 and/or 27-aminocholesterol, or a sterol 27-hydroxylase stimulant, is administered in a restenosis preventing and/or reducing amount. The invention also includes a method for treating cancer using 27-hydroxycholesterol.

22 Claims, No Drawings

ADMINISTRATION OF A 27-HYDROXYCHOLESTEROL OR RELATED COMPOUND OR STEROL-27-HYDROXYLASE STIMULANT TO PREVENT RESTENOSIS FOLLOWING VASCULAR ENDOTHELIAL INJURY

The subject application is a Continuation-In-Part of application No. 08/159,226, filed on Nov. 30, 1993, now U.S. Pat. No. 5,376,652, which has been allowed and is hereby incorporated in its entirety.

BACKGROUND OF THE INVENTION

1. Technical Field

The subject invention relates to methods of using 27-hydroxycholesterol, sterol-27-hydroxylase, and related compounds in the prevention of restenosis. The subject invention also relates to methods of using 27-hydroxycholesterol in the treatment of cancer.

2. Background Information

Various surgical bypass and angiographic procedures are routinely employed for increasing blood flow to an organ, usually the heart. These operative and non-operative procedures injure, to a greater or lesser extent, the interior wall of the lumen of the blood vessel at the target site. This endothelial injury often leads through a cascade of events to restenosis. For example, balloon, laser or rotameter angioplasty, in which a catheter is inserted into the arterial system to place a balloon, laser or blade at the stenosis, is quite successful in widening a narrowed area of a blood vessel lumen. However, endothelial injury occurs at the site of the lesion, leading to restenosis in an estimated 20–40% of patients.

It has been shown in animals that endothelial injury initiates a process that leads to narrowing of the injured artery (stenosis), and this model is related and is used to study the events that occur following endothelial injury.

The major current theory for explaining restenosis is that once the endothelial cells are injured or removed by the invasive procedure, circulating platelets cover the denuded areas and release potent growth factors, such as platelet derived growth factor, which stimulate the growth and migration of underlying smooth muscle cells. Other growth factors, such as fibroblast growth factors, have also been implicated. For these reasons, anti-growth factors are being evaluated for the prevention of atherosclerosis.

Many factors are thought to potentially participate in restenosis. Further, hemodynamic forces responsible for the original lesion are not generally alleviated by angioplasty and may be aggravated at plaque disruption. The thrombo-resistant nature of the arterial lumen is reduced due to the generation of markedly thrombogenic surfaces of complex geometrical configuration, and changed permeability characteristics permitting possible direct interaction between blood-borne elements such as the aforementioned platelets and the arterial lumen. In summary, the surgical and angiographic procedures necessarily result in injury to vessel walls, which results in restenosis in 20–40% of patients.

27-hydroxycholesterol (cholest-5-ene-3β,27-diol) is normally present in biological fluid after neonatal life. Recently, the IUB changed certain rules of nomenclature, and the compound now referred to as 27-hydroxycholesterol was previously called 26-hydroxy-cholesterol. Two methyl groups are attached to carbon number 25 of cholesterol, but only one can be enzymatically hydroxylated, which was previously named carbon number 26, but is now named as carbon number 27.

U.S. Pat. No. 4,427,688 by Javitt describes the administration of 26-hydroxycholesterol (sic., 27-hydroxycholesterol) and various derivatives and analogs thereof for reducing cholesterol synthesis and/or cholesterol accumulation in the body tissues; hence, teaching the use of 27-hydroxycholesterol compounds for the treatment of atherosclerosis. Thereafter, as disclosed in U.S. Pat. No. 4,939,134, Javitt, et al. discovered that 27-aminocholesterol, and certain amino-substituted analogs and derivatives thereof, are more potent inhibitors of cholesterol synthesis and accumulation than 27-hydroxycholesterol.

Javitt filed Japanese Application 107488/82 in 1982, published as 019206/91 on Nov. 14, 1991 ("JPA"), largely corresponding in disclosure to U.S. Pat. No. 4,427,688 with insertion of additional information for further supporting use of 27-hydroxycholesterol in treatment of atherosclerosis. The JPA notes that Kandutsch, et al., *Science*, 201, 498 (1978) mentioned that oxygenated cholesterol has an inhibitory effect on the proliferation of fibroblasts and lymphocytes in vitro, perhaps by inhibiting HMG CO-A reductase, the rate-limiting enzyme in cholesterol biosynthesis, which is consistent with the idea that cholesterol is essential to cell proliferation. Javitt tested this theory by seeding hamster aortic smooth muscle cells at low density in culture wells and coulter counting control and 27-hydroxycholesterol exposed cells six days later. The 27-hydroxycholesterol at the tested concentration inhibited the proliferation by about 50%. Although a potential lead, in vitro muscle cell proliferation inhibition, in itself, does not teach nor suggest the use of the same substance for preventing restenosis in vivo. Indeed, some have interpreted the inhibitory effect by oxysterols on vascular smooth muscle cells as a toxic effect. Zhou, et al., *Proc. Soc. Exp. Biol. Med.*, 202:75–80; Nassem, et al., *Biochem. Internat.*, 14:71–84. Also see Baranowski, et al., *Atherosclerosis*, 41:255–260. Further, it has been recently reported that high doses of Lovastatin, a potent cholesterol lowering drug, in a randomized, double blind placebo controlled trial, did not decrease restenosis six months following percutaneous transluminal coronary angioplasty, although the Lovastatin did markedly decrease LDL-cholesterol level, as expected. Thus, as of today, the cholesterol lowering biological activity of a drug, while perhaps indicating potential use in the treatment of atherosclerosis, is not predicative nor suggestive of use for combating restenosis. As discussed above, restenosis is a multi-faceted phenomena, distinct from atherosclerosis, and the mechanism of which is, at best, only partially understood.

All U.S. patents and publications referred to herein are hereby incorporated by reference.

SUMMARY OF THE INVENTION

Hereinafter, the currently accepted nomenclature for the sterol nucleus involved herein, 27-hydroxycholesterol, is employed. It is understood that this compound is identical to the compound named 26-hydroxycholesterol in the prior art discussed above as well as other prior art.

It has now been found that 27-hydroxycholesterol effectively reduces restenosis following injury to the blood vessel lumen which occurs when the lumen is widened by catheter procedure. Therefore, it is an object of the present invention to provide a method for reducing the instance of restenosis which occurs following surgical by-pass procedures and percutaneous angiographic procedures. Further, it is expected that related compounds such as 25-, 26-, and/or 27-aminocholesterol will have a similar effect on the blood vessel lumen.

It is also expected that certain metabolites of 27-hydroxycholesterol, produced by the continuing activity of sterol 27-hydroxylase, are also biologically active. In particular, it is believed that 3β-hydroxy-5-cholestenoic acid, a metabolite of 27-hydroxycholesterol, may potentiate the activity of 27-hydroxycholesterol by slowing the rate at which the latter is metabolized.

Another object of the present invention is to provide a method for reducing the occurrence of restenosis after balloon, laser or rotameter angioplasty. A further aspect of the present invention involves the administration of a 27-hydroxycholesterol, or related compound immediately following injury to the lumen of a blood vessel as a result of a mechanical widening thereof, and to continue to administer said compound to a patient in a maintenance dosage to prevent restenosis.

In still another embodiment of this invention, the 27-hydroxycholesterol or related compound is administered orally or intravenously, preferably intravenously dissolved in an aqueous solution of a β-cyclodextrin such as 2-hydroxypropyl-β-cyclodextrin.

In another embodiment of the present invention, a sterol 27-hydroxylase stimulant is administered to thereby increase the synthesis of 27-hydroxycholesterol in the vascular tissue. This aspect of the invention is based on a finding of sterol 27-hydroxylase activity in aortic endothelial cells.

In an additional embodiment of the present invention, 27-hydroxycholesterol is administered to a patient in order to inhibit the proliferation of various types of cancer-causing tumor cells.

Other objects of the invention will be apparent to the skilled artisan from the detailed description of the invention hereinbelow.

DETAILED DESCRIPTION OF THE INVENTION

The compounds for use in the practice of the present invention are, in general, known in the art, and may be represented by the following formula:

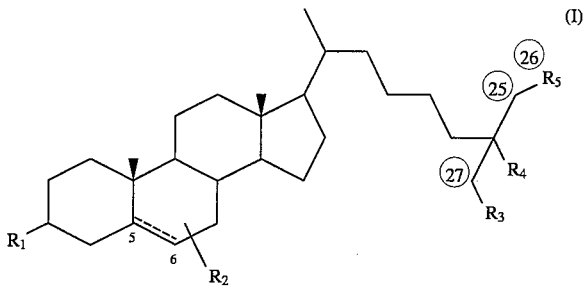

wherein $R_1$ is hydroxyl or keto; $R_2$ is hydrogen, hydroxyl or keto; $R_3$ is hydroxyl, carboxyl, hydrogen or amino; $R_4$ and $R_5$ are hydrogen or amino; with the provisos that when $R_3$ is hydroxyl both $R_4$ and $R_5$ are hydrogen, and when $R_3$ is not hydroxyl, at least one of $R_3$, $R_4$ and $R_5$ is amino (—$NH_2$) and the other(s) of them are hydrogen or amino, and pharmaceutically acceptable derivatives and salts thereof. In formula (I), $R_3$ is substituted at position 27.

A preferred group of compounds for use in the practice of the present invention are those within formula (I) wherein the 27-position ($R_3$) is substituted by hydroxyl or amino, and each of $R_4$ and $R_5$ is hydrogen.

At this time, the most preferred compound for use in the inventive process for reducing and/or preventing restenosis is 27-hydroxycholesterol.

Other compounds usable herein include 25-aminocholesterol, 26-aminocholesterol, 27-aminocholes-terol, 27-nor-25-amino-cholesterol, 25-amino-cholesta-4,6-dien-3-one, 25-amino-cholest-4-en-3-one, 22-amino-cholest-5-en-3,B-ol, 20-amino- 25,26,27-trinorcholest-5-ene-3,B-ol, 25-amino-cholesta-3,5-dien-7-one.

For administration to a patient, the compounds of the present invention can be provided, per se, or as the mono and diesterified derivatives and other pharmaceutically acceptable derivatives thereof such as the mono- and diethers. Most usually, fatty acid, the same or analogous to those naturally occurring, would be used to form the esters, but other inorganic and organic esters, such as acetates, the sulfates, carbonates and glucuronides, routinely employed in preparing pharmaceutically acceptable esters, could be used. Esterification and/or etherification can occur at the 3- and/or 27-position, or at carbon positions 6 or 7 when $R_2$ is hydroxyl. Aryl and/or alkyl ethers, such as methyl, ethyl or cycloalkyls (i.e., cyclopentyl ethers) are contemplated. Furthermore, acid salts and various substituted compounds, for example, those containing elements such as fluorine commonly used in modification of steroid-type compounds, as long as pharmaceutically acceptable, can be used.

Administration can be through the use of liquid and solid formulations and also through the use of injectables, such as intravenous injectables, wherein conventional pharmaceutical carriers would be employed.

Suitable pharmaceutical preparations include tables, capsules, oral liquids and parenteral injectables. Tablet and capsule formulations can be employed utilizing conventional diluents, excipients and the like such as lactose in conventional capsule and tablet-making procedures. Parenteral injections could employ solvents conventionally used with lipid-soluble materials, or a salt of the sterol could be prepared, at least some of which should be soluble in aqueous solvents.

It has been difficult to form aqueous solutions of the compounds found herein for parenteral administration. None of the vehicles commonly used to solubilize steroids and bile acids, such as propylene glycol, ethanol, dimethyl sulfoxide or dimethyl formamide, is able to maintain solubility when diluted with aqueous media. As disclosed by DeCaprio, Yen and Javitt, *Journal of Lipid Research*, Vol. 33, pp. 441–443, 1992, 27-hydroxycholesterol and it is expected the related compounds involved herein, can be stabilized in aqueous media by inclusion of a cyclodextrin therein. It has been theorized that the cyclic structure of the cyclodextrin provides a lipophilic interior in which compounds that have limited aqueous solubility will form a soluble complex. The β-cyclodextrins usable for this purpose are known in the art and are inclusive of the 2-hydroxypropyl-β-cyclodextrin described by DeCaprio, et al., supra. Other non-toxic cyclodextrins would be usable.

The compounds of the present invention are administered in amounts ranging from 10 mg/kg to 100 mg/kg, preferably about 20 mg/kg to 40 mg/kg, 1 to 3 times a day.

In one embodiment of the present invention, the compound of the present invention is administered as a bolus, employing a dosage toward the upper end of the above dosage range, immediately prior to, during and/or following the blood vessel lumen widening, followed by reduction to a maintenance dosage toward the lower end of the above dosage range. It is contemplated that the maintenance dosage would continue over a prolonged period of time of, for example, 1 to 5 months.

The following non-limiting example is provided to illustrate the above-described aspect of the present invention:

EXAMPLE 1

VASCULAR INJURY MODEL

New Zealand white rabbits weighing 2.6 to 5.1 kgs were anesthetized with intramuscular ketamine 35 mg/kg. Additional injections of ketamine (100 mg/cc) and xylazine (20 mg/cc) in a 50/50 mixture were given as necessary in 1 ml increments. Keflin (Eli Lilly & Co.), 30/mg/kg was given intravenously (IV). A longitudinal incision was made on the medial aspect of the distal hind limb to expose the greater saphenous artery. Arteriotomy was performed, and a 3-F Fogarty embolectomy catheter (Edwards Laboratories, Santa Ana, Calif.) was introduced and advanced to the level of the diaphragmatic abdominal aorta. The catheter was withdrawn from the abdominal aorta with the balloon inflated to a pressure of about 20 mmhg. This maneuver was repeated for a total of three passes. The catheter was removed, and the saphenous artery was ligated. The wound was irrigated and closed with 4-0 Dexon suture.

SPECIMEN ANALYSIS

The abdominal aortas were fixed by perfusion with glutaraldehyde at physiological pressure via a catheter (14G Intracath) placed in the left ventricle. One micron longitudinal sections of epoxy embedded aorta specimens were cut, stained, and computer imaged. The entire intimal and medial areas in more than 2 sections per specimen were measured using Lucida computer calculation (Micro Brightfield, Inc.). The degree of intimal thickening was determined by calculating the intimal to medial area (I/M) ratio. Statistical significance of the difference in intimal/medial ratio between groups was calculated using student t-test.

RUN I

Using the above procedure, a study was carried out employing five control balloon injury rabbits and two groups, each of five balloon injury test rabbits, for receiving 27-hydroxycholesterol or suramin, the latter having been shown to inhibit intimal proliferation.

On the day before surgery, 10 mg 27-hydroxycholesterol dissolved in 1.0 ml of 45% aqueous solution of 2-hydroxypropyl-β-cyclodextrin (HPBCD) was administered intravenously to one group of five test rabbits. Suramin was administered to the other test group. bFGF was administered throughout the testing period.

On the day of surgery, a short time prior to the balloon angioplasty, the five test rabbits were administered another 5 mg of 27-hydroxycholesterol in 0.5 ml HPBCD, and the same dosage was administered to each of the five test rabbits twice a day on days 1 to 14 following the day of balloon angioplasty, in the form of 5 mg 27-hydroxycholesterol in 0.5 ml 45% HPBCD twice a day. On day 14, the above specimen analysis was carried out on the fifteen rabbits, with the following results.

| QUANTITATIVE HISTOLOGICAL EVALUATION OF ARTERIAL WALL 14 DAYS | | |
|---|---|---|
| | Mean Intima/Media Ratio[1] | |
| | 5-DAY | 14-DAY |
| Control (28 rabbits) | $0.094 \pm 0.006$ | $0.5542 \pm 0.024$ |
| Suramin Administration | | $0.4089 \pm 0.034$[2] |
| 27-OHcholesterol Administration | | $0.4872 \pm 0.0238$ |

[1]Ratio of thicknesses of intima and media of artery wall
[2]$p < 0.05$

This run suggests an improved intima/media ratio through the administration of 27-hydroxycholesterol. However, the results were not as good as with suramin and when calculated, the difference between the control group and the 27-hydroxycholesterol group was not statistically significant. With a suggestion of utility, a further run was carried out with increased 27-hydroxycholesterol dosage.

RUN II

Control (vehicle alone) and 27-hydroxycholesterol test rabbits were used as in Run I, with the exception that each test rabbit received 100 mg 27-hydroxycholesterol dissolved in 5.0 ml 45% HPBCD subcutaneously on the day before surgery, the day of surgery and on days 1 to 14 following surgery.

| QUANTITATIVE HISTOLOGICAL EVALUATION OF ARTERIAL WALL 14 DAYS | |
|---|---|
| | Mean Intima/Media Ratio |
| Control (28 rabbits) | $0.5209 [\pm .001]$ |
| Test (20 rabbits) | $0.2880 [\pm .024]$ |

The 27-hydroxycholesterol reduced degree of intimal thickening by nearly ½ as compared with the control group.

In a second aspect of the present invention, a sterol-27-hydroxylase stimulant is administered to increase the sterol-27-hydroxylase activity present in vascular tissue, the presence thereof in vascular tissue being heretofore unknown. In this manner, not only is the available amount of 27-hydroxycholesterol enhanced since it is one of the major metabolites from sterol-27-hydroxylase activity, but the 27-hydroxycholesterol is produced in the cells at the location where it is best utilized by the body in reducing and/or preventing restenosis.

The sterol 27-hydroxylase activity in bovine aortic endothelial (BAE) cells in culture has been compared with that in Hep G2 cells and in Chinese hamster ovary (CHO) cells using identical culture conditions. The total enzyme activity of BAE cells (3.0 nmol/72 h/mg cell protein) was comparable with that of Hep G2 cells (4.0 nmol/72 h/mg protein), and both values were significantly greater than that in CHO cells (0.002 nmol/72 h/mg protein). The enzyme was identified in BAE cells by Western blotting using an antibody of proven specificity, and its metabolites 27-hydroxycholesterol and 3β-hydroxy-5-cholestenoic acid were identified by mass spectrum analysis. The presence of the enzyme in endothelium provides a mechanism for providing the biologic effects of 27-hydroxycholesterol in vascular tissue.

EXAMPLE 2

CELL CULTURE

Bovine aortic endothelial (BAE) cells obtained from a slaughterhouse were plated at low density ($2 \times 10^5$ cells/cm$^2$)

in 100-mm dishes and were grown to confluence in Dulbecco's modified Eagle medium (DMEM) supplemented with 10% fetal bovine serum (FBS), 50 units/ml penicillin, and 50 units/ml streptomycin at 37° C. in a 5% $CO_2$ atmosphere. The confluent monolayer was rinsed once with Hank's balanced salt solution, and 4 ml of DMEM containing 10% dilapidated FBS and either 20 µM cholesterol dissolved in 2-hydroxypropyl-β-cyclodextrin or an equivalent amount of vehicle alone was added to each dish. Hep G2 cells and Chinese hamster ovary cells (CHO) were cultured under identical conditions and for the same length of time. At 24-h intervals, the media and cells were harvested. The medium obtained from each dish was analyzed for metabolites. Cells were pooled for immunoblot analysis.

WESTERN BLOTTING

Samples were subjected to electrophoresis on a 10% SDS-polyacrylamide gel and were transferred onto a nitrocellulose membrane by an electrophoretic technique. Antibody was raised in rabbits against residues 15 to 28 of the 27-hydroxylase protein. Visualization was accomplished using an alkaline phosphatase-conjugated goat and antirabbit antibody followed by the Rad-free kit for calorimetric detection of Western blots (Schleicher & Schuell, Keene, N.H.).

Several attempts were made to detect the 56-kb 27-hydroxylase protein in mitochondria prepared from BAE cells, but despite the use of protease inhibitors, the predominant immunoreactive band was detected at 35 kd, with occasionally a faint band at 56 kd. Boiling freshly harvested whole cells in loading buffer appears to have prevented proteolysis.

GLC-MS ANALYSIS

Sample Preparation

To 1 ml of harvested medium, internal standards (500 ng each) of deuterated 27-hydroxycholesterol, 3β-hydroxy-5-cholestenoic acid (prepared by Jones oxidation of the 3-monoacetate of the deuterated 27-hydroxysterol), and $^{13}C$-3β-hydroxy-5-cholenoic acid were added and allowed to equilibrate for 30 min at room temperature. Following acidification and extraction into ethyl acetate, the dried residue was saponified. In some studies, solvolysis was also done prior to extraction. The dried extract was applied to a silica gel G TLC plate together with authentic standards in parallel lanes; after development (chloroform/acetone, 97:3), the standards were visualized by spraying with phosphomolybdic acid and the appropriate areas of the plate were removed for elution of 27-hydroxy-cholesterol and the $C_{27}$ and $C_{24}$ acids. The diacetate of 27-hydroxycholesterol and methyl acetates of the $C_{27}$ and $C_{24}$ acids were then prepared using dimethoxy-propane/HCl for methylation and pyridine/acetic anhydride for acetylation. It was found that complete methylation of the $C_{27}$ acid with dimethoxypropane/HCl took longer than that of the $C_{24}$ acid. Therefore, methylation was allowed to proceed at room temperature overnight (approximately 18 h). Formation of a 3-methoxy derivative by this prolonged methylation procedure was not detected.

ISOTOPE RATIO MASS SPECTROMETRY

Using a Hewlett-Packard GLC-MS (Model #5890-5970) and a fused silica column (CP-sil 19 CB, 0.25 mm i.d., 25 m length; Chrompack, Raritan, N.J.), the appropriate TLC fractions were injected in the splitless mode with temperature programming from 260° C. to 270° C. at 1.0° C./min and a column head pressure of 5 psi.

To quantify 27-hydroxycholesterol the detector was programmed in the simultaneous ion monitoring mode for m/z 426 [mol ion diacetate=486–60 (acetate)] and m/z 430, and the amount of endogenous 27-hydroxycholesterol was calculated from the respective areas. For the $C_{27}$ acid, the ion pair that was used was m/z 412 [methyl ester acetate mol ion=476–60 (acetate)] and m/z 416, and for the $C_{24}$ acid, m/z 370 [mol ion methyl ester acetate=430–60 (acetate)] and m/z 373.

RESULTS

Both the spectra and the retention times of 27-hydroxycholesterol and of 3β-hydroxy-5-cholestenoic acid isolated from the sterol-free medium that was in contact with BAE cells for 72 h are identical to authentic standards of the diacetate and methyl ester diacetate derivatives, respectively.

After the identity of these compounds was established by complete spectrum analysis, an isotope ratio program was used to compare their rates of synthesis in sterol-free and cholesterol-supplemented medium. As shown in Table 1, medium containing 20 nmol/ml of cholesterol yielded a much greater amount of metabolites than sterol-free medium. At 72 h, the metabolites represented approximately 5.8% of the cholesterol added to the medium [(1.029+0.211)–(0.103+0.079)×100÷20]. Although the amount of 27-hydroxycholesterol in the medium was relatively constant from 24 to 72 h, a progressive increase in the amount of 3β-hydroxy-5-cholestenoic acid occurred. For BAE cells maintained in nonsupplemented medium, the proportion of $C_{27}$ acid rose from 12% at 24 h to 43% at 72 h. In contrast, although the absolute amount of the $C_{27}$ bile acid that was synthesized was greater in cholesterol-supplemented medium, it represented only 3.8% of total metabolite at 24 h and increased to 17% at 72 h.

The activity of sterol 27-hydroxylase in BAE cells was compared with that in Hep G2 and CHO cells using the cholesterol-supplemented medium. As shown in Table 2, the amount of 27-hydroxycholesterol in the medium collected from BAE cells at 72 h was greater than that from Hep G2 cells. The amount present in medium from CHO cells was below the limit of detection (10 ng per assay).

The medium from CHO cells always contained a small amount of 3β-hydroxy-5-cholenoic acid, which was much less than that found in the medium from Hep G2 or BAE cells.

Because Hep G2 cells synthesize 3β-hydroxy-5-cholenoic acid from 27-hydroxycholesterol, the medium from all the cell lines was analyzed for this derivative before and after solvolysis. No increase in the yield of 3β-hydroxy-5-cholestenoic acid was obtained after solvolysis of media derived from Hep G2 or the other cell lines. Medium from Hep G2 cells was found to contain 3β-hydroxy-5-cholenoic acid, which increased in amount following solvolysis.

Since all the metabolic products are derived from the sterol 27-hydroxylase activity of the cells, the total amounts produced by Hep G2 and BAE cells are comparable and are much greater than that from CHO cells.

TABLE 1

Synthesis of 27-hydroxycholesterol and
3β-hydroxy-5-cholestenoic acid by BAE Cells: Time course
and effect of cholesterol added to the medium

| Culture Medium | 24 h | 48 h | 72 h |
|---|---|---|---|
| | 27-hydroxycholesterol (pmol/ml medium) | | |
| Delipidated FBS[a] (n = 4)[b] | 89 ± 12[c] | 98 ± 11 | 103 ± 9 |
| +20 nmol/ml cholesterol | 1089 ± 111 | 1064 ± 161 | 1029 ± 99 |
| | 3β-hydroxy-5-cholestenoic acid (pmol/ml medium) | | |
| Delipidated FBS | 11.9 ± 1.3 | 32.0 ± 1.9 | 78.6 ± 11 |
| +20 nmol/ml cholesterol | 42.5 ± 6.1 | 112 ± 12.4 | 211 ± 48.3 |

[a] Delipidated fetal bovine serum
[b] Number of dishes
[c] Mean ± standard deviation

TABLE 2

Comparison of Sterol 27-hydroxylase activity
in BAE, Hep G2 and CHO cells

| Cells[a] | Metabolites Derived from Sterol 27-Hydroxylase (pmol/mg/cell protein) | | | |
|---|---|---|---|---|
| | 27OH-chol.[b] | 3βOH-5-cholest. a. | 3βOH-5-cholen. a. | Total |
| BAE (n = 6)[c] | 2555 ± 348 | 474 ± 118 | not detected | 3029 |
| HEP G2 (n = 6) | 1622 ± 291 | 471 ± 126 | 1940 ± 270[d] | 4033 |
| CHO (n = 3) | not detected | 2 ± 1 | not detected | 2 |

[a] All cells were maintained for 72 h in DMEM enriched with 10% delipidated FBS containing 20 μM cholesterol.
[b] 27OH-chol = 27-hydroxycholesterol; 3βOH-cholest. a. = 3β-hydroxy-5-cholestenoic acid; 3βOH-cholen. a. = 3β-hydroxy-5-cholenoic acid.
[c] Number of dishes.
[d] Mean value of 2 dishes after solvolysis.

From the above, the positive effects of this invention on restenosis can be provided by stimulating the sterol 27-hydroxylase activity of the vascular endothelium. Various stimulatory mechanisms are known, such as by the administration of steroid hormones, such as the naturally-occurring sex hormones estrogen and testosterone.

The skilled artisan will be able to select other naturally-occurring and synthetic steroid hormones for use in providing a sterol 27-hydroxylase stimulant effect.

An additional experiment was carried out in order to determine the effects of 27-hydroxycholesterol and 3β-hydroxy-5-cholestenoic acid or the proliferation of rabbit, smooth muscle cells. This experiment is presented below:

Effect of 27-Hydroxycholesterol and 3β-Hydroxy-5-Cholestenoic Acid on Rabbit Smooth Muscle Cell Proliferation Using 96 well microtiter plates, 5000 cells were plated in each well and, after synchronization in Dulbecco's modified Eagle's medium containing 0.1% fetal bovine serum (FBS), the medium was removed and replaced with medium containing 5% dilapidated FBS and the vehicle containing varying concentrations of either 27-hydroxycholesterol or 3β-hydroxy-5-cholestenoic acid. Cell proliferation at 24 hr was measured using formazan formation from MTS which is known to correlate with the number of cells present in each well. At 24 hr, the optical density of wells containing 20 μm 27-hydroxycholesterol was 0.350±0.021 and for those containing 3β-hydroxy-5-cholestenoic acid 0.357±0.22. Compared to control wells (optical density= 0.402±0.037) a significant reduction (p<0.01) occurred indicating that both compounds have an antiproliferation effect directed against rabbit smooth muscle.

Furthermore, an experiment was also performed in order to examine the effect of 27-hydroxycholesterol on the proliferation of cells derived from the rat aorta and the human femoral artery. This experiment is presented below:

Effect of 27-Hydroxycholesterol on Proliferation of Smooth Muscle Cells Derived from Rat Aorta and Human Femoral Artery (Laboratory of Dr. A. Corsini, Institute of Pharmaceutical Sciences, Milan, Italy Smooth muscle cells were cultured according to Ross (*J. Cell. Biol.*, 50:172, 1971) from the intimamedial layer of male Sprague-Dawley rats (200–250 g). Cells were grown in monolayers at 37° C. in a humidified atmosphere of 5% $CO_2$ in MEM supplemented with 10% FBS, 100 U/ml penicillin, 0.1 mg/ml streptomycin, 20 nM tricine buffer and 1% non-essential amino acid solution (Corsini et al, *Atherosclerosis*, 101:117, 1993). The medium was changed every third day. Cells were used between the 4th and 10th passage. Cell viability was assessed by trypan blue exclusion. Smooth muscle cells were identified for growth behavior, morphology, and using monoclonal antibody specific for α-actin, using the isoform typical for smooth muscle cells. Human vascular myocytes were taken from a human femoral artery and grown under the same culture conditions.

Smooth muscle cells derived from rat aorta were seeded at a density of $2\times10^5$ and those from the femoral artery at a density of $5\times10^4$. After synchronization in MEM containing 0.4% FBS for 48 hr, the medium was replaced with 10% FBS and 27-hydroxycholesterol added. Cell proliferation was determined at 72 hr either by trypsinization of the monolayer and counting in a model ZM Coulter Counter or by incorporation of tritiated thymidine after a 3 hr incubation.

The results are presented in table form below:

| 27-Hydroxycholesterol Concentration in | Growth Smooth Muscle Cells Percent of Control Growth | |
|---|---|---|
| Medium (μM) | Rat Aorta | Human Femoral A |
| none (control) | 100 | 100 |
| 1.0 | 90 | 100 |
| 5.0 | 40* | 53* |
| 7.5 | 18 | not done |

*p < 0.01

The above-two experiments and data relating thereto provide a mechanism for the reduction that occurs in neointimal hyperplasia following endothelial injury or denudation (i.e., prevention of restenosis). Thus, these additional experiments establish that both 27-hydroxycholesterol and 3β-hydroxy-5-cholestenoic acid inhibit smooth muscle proliferation and presumably therefore migration of cells into the intima. Smooth muscle cells by both migration and proliferation account for the bulk of the neointima which causes restenosis.

Another embodiment of the present invention relates to the use of 27-hydroxycholesterol in the treatment of different types of cancer, for example, human metastatic colon cancer.

It is well-known that a major cause of death from cancer of the colon is the spread of the cancer cells to the liver. Thus, even after the removal of the primary lesion in the colon, the disease progresses because of continued growth of the tumor cells in the liver with cachexia and death.

Current treatment of metastatic colon cancer includes the infusion of 5-FU (5-fluorouracil) into the portal vein going to the liver.

Because of the inhibitory effect of 27-hydroxycholesterol on a human colon tumor cell line, it is feasible to infuse 27-hydroxycholesterol intravenously into the portal vein or hepatic artery of a patient, although systemic therapy might be just as effective. Additionally, administration via a peripheral vein or subcutaneously or intramuscularly may also be possible. It may, perhaps, also be possible to administer 27-hydroxycholesterol orally as a disuccinate derivative.

In addition to use in the treatment of colon cancer, 27-hydroxycholesterol may also be utilized to treat other metastatic cancers where the metastasis is thought to be confined to the liver. Thus, occasionally, metastatic breast cancer, for example, may also be treated by using 27-hydroxycholesterol. Such therapeutic treatment may be applicable to human use as well as to veterinary use.

The unique value of 27-hydroxycholesterol, in contrast to 5-FU and other chemotherapeutic agents, is the selective effect that can be obtained in only killing the tumor cells.

The rationale for this statement is based on the knowledge that only the normal liver cells have a metabolic pathway for rapidly metabolizing the 27-hydroxycholesterol to normal bile acids which, in the usual concentrations, have no toxic effects. In contrast, tumor cells have no known pathway for metabolizing 27-hydroxycholesterol. Thus, a tumorcidal dose will accumulate only in tumor cells, but the normal liver cells will not be affected.

Moreover, the finding that 27-hydroxycholesterol also inhibits the growth of tumor cells, particularly HCT-8, at a concentration that has been achieved by parenteral administration to rabbits provides further evidence for a new unique chemotherapeutic use for this remarkable compound.

It should also be noted that 27-hydroxycholesterol may be administered with other compounds, such as 3β-hydroxy-5-cholestenoic acid, in the treatment of cancer. As noted previously, it is thought that 3β-hydroxy-5-cholestenoic acid slows down the metabolism of 27-hydroxycholesterol.

An experiment which demonstrated the ability of 27-hydroxycholesterol to inhibit cellular proliferation is presented below:

Effect of 27-Hydroxycholesterol on Cell Proliferation of Tumor Cell Lines (Studies Done in Laboratory of Dr. Joseph Bertino, Program Chairman, Molecular Pharmacology and Therapeutics Sloan-Kettering Institute for Cancer Research, New York, N.Y.)

| Tumor Cell Line | Concentration of 27-Hydroxycholesterol Yielding 50% Growth Inhibition |
|---|---|
| 2. L1210 cells (mouse leukemia cell line): | $1.2 \times 10^{-6}$M |
| 3. K-12 cells (at adenocarcinoma line): | $3.7 \times 10^{-6}$M |
| 4. HCT-8 (human colon carcinoma) | $11.5 \times 10^{-6}$M |

Conventional methods of cell culture were utilized in this experiment.

As will be noted, the concentrations at which 50% inhibition of cell growth occurs are not extremely potent. However, because 27-hydroxycholesterol is not toxic to normal cells and high concentrations can be achieved by intraportal administration, the range that is indicated as therapeutic in the cell culture studies can be exceeded. (See Table below which indicates the high concentration of 27-hydroxycholesterol found in treated rabbits as well as the plasma concentration of the compound.)

TABLE

| Plasma Concentration and Distribution of 27-Hydroxycholesterol | | | |
|---|---|---|---|
| Control | | Treated | |
| Rabbit # | μM | Rabbit # | μM |
| 2016 | 0.55 | 342 | 5.25 |
| 345 | 0.63 | 343 | 5.20 |
| 384 | 0.56 | 385 | 4.50 |
| 386 | 0.70 | 387 | 2.34 |
| 388 | 0.59 | 390 | 11.2 |
| Means ± S.D. | 0.61 ± 0.6 | | 5.7 ± 3.3 |

| Distribution of Plasma 27-Hydroxycholesterol Nonfasted Rabbits | | | | | |
|---|---|---|---|---|---|
| Control # | | | Treated % | | |
| VLDL | LDL | HDL | VLDL | LDL | HDL |
| 3 | 53 | 44 | 34 | 55 | 11 |

What is claimed is:

1. In a process wherein in a mammal, a therapeutic procedure is carried out to reduce or remove a stenosis present within a lumen of a blood vessel, the improvement to prevent restenosis which comprises administering to the mammal a restenosis preventing amount of a compound of formula (I):

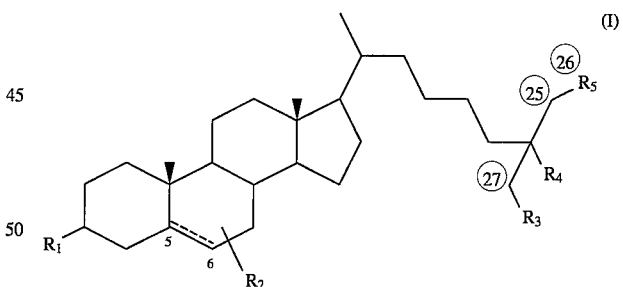

wherein $R_1$ is hydroxyl or keto; $R_2$ is hydrogen, hydroxyl or keto; $R_3$ is hydroxyl, carboxyl, hydrogen or amino; $R_4$ and $R_5$ are hydrogen or amino; with the provisos that when $R_3$ is hydroxyl both $R_4$ and $R_5$ are hydrogen and when $R_3$ is not hydroxyl, at least one of $R_3$, $R_4$ and $R_5$ is amino ($-NH_2$) and the other(s) of them are hydrogen or amino, and pharmaceutically acceptable derivatives and salts thereof.

2. In a process wherein in a mammal, a therapeutic procedure is carried out to reduce or remove a stenosis present within a lumen of a blood vessel, the improvement to reduce the degree of restenosis which comprises administering to the mammal a restenosis reducing amount of a compound of formula (I):

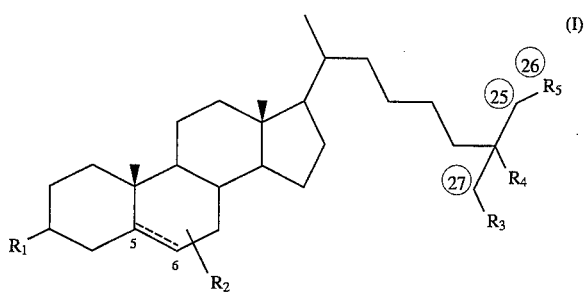

wherein $R_1$ is hydroxyl or keto; $R_2$ is hydrogen, hydroxyl or keto; $R_3$ is hydroxyl, carboxyl, hydrogen or amino; $R_4$ and $R_5$ are hydrogen or amino; with the provisos that when $R_3$ is hydroxyl both $R_4$ and $R_5$ are hydrogen and when $R_3$ is not hydroxyl, at least one of $R_3$, $R_4$ and $R_5$ is amino ($-NH_2$) and the other(s) of them are hydrogen or amino, and pharmaceutically acceptable derivatives and salts thereof.

3. The process of claim 1, wherein $R_3$ is hydroxyl or amino and each of $R_4$ and $R_5$ is hydrogen.

4. The process of claim 2, wherein $R_3$ is hydroxyl or amino and each of $R_4$ and $R_5$ is hydrogen.

5. The process of claim 1, wherein the compound of formula (I) administered is 27-hydroxycholesterol.

6. The process of claim 2, wherein the compound of formula (I) administered is 27-hydroxycholesterol.

7. The process of claim 1, wherein the compound of formula (I) is administered in a pharmaceutically acceptable carrier comprising an aqueous medium containing a pharmaceutically acceptable cyclodextrin in sufficient amount to stabilize the compound of formula (I) in the aqueous medium.

8. The process of claim 2, wherein the compound of formula (I) is administered in a pharmaceutically acceptable carrier comprising an aqueous medium containing a pharmaceutically acceptable cyclodextrin in sufficient amount to stabilize the compound of formula (I) in the aqueous medium.

9. The process of claim 1, wherein the therapeutic procedure is a surgical procedure.

10. The process of claim 2, wherein the therapeutic procedure is a surgical procedure.

11. The process of claim 1, wherein the therapeutic procedure is balloon, laser or rotameter angioplasty.

12. The process of claim 2, wherein the therapeutic procedure is balloon, laser or rotameter angioplasty.

13. The process of claim 1, wherein the therapeutic procedure is balloon angioplasty.

14. The process of claim 2, wherein the therapeutic procedure is balloon angioplasty.

15. The process of claim 1, wherein the compound of claim 1 is administered in an amount of about 10 to 100 mg/kg 1 to 3 times a day.

16. The process of claim 2, wherein the compound of claim 1 is administered in an amount of about 10 to 100 mg/kg 1 to 3 times a day.

17. The process of claim 1, wherein the compound of formula (I) is administered as the compound itself or as a mono- or di-ester, or mono- or di-ether thereof.

18. The process of claim 2, wherein the compound of formula (I) is administered as the compound itself or as a mono- or di-ester, or mono- or di-ether thereof.

19. The process of claim 1 wherein the compound of formula (I) is administered prior to, during and/or after the therapeutic procedure.

20. The process of claim 2 wherein the compound of formula (I) is administered prior to, during and/or after the therapeutic procedure.

21. The process of claim 1 wherein the compound of formula (I) is administered after the therapeutic procedure.

22. The process of claim 2 wherein the compound of formula (I) is administered after the therapeutic procedure.

* * * * *